(12) United States Patent
Chassot et al.

(10) Patent No.: US 7,125,428 B2
(45) Date of Patent: Oct. 24, 2006

(54) 1,3-DIHYDROXYBENZENE DERIVATIVES AND COLORANTS CONTAINING SAID COMPOUNDS

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 253 days.

(21) Appl. No.: 10/416,048

(22) PCT Filed: Jan. 28, 2002

(86) PCT No.: PCT/EP02/00850

§ 371 (c)(1),
(2), (4) Date: May 3, 2003

(87) PCT Pub. No.: WO02/096901

PCT Pub. Date: Dec. 5, 2002

(65) Prior Publication Data

US 2004/0016063 A1    Jan. 29, 2004

(30) Foreign Application Priority Data

May 25, 2001   (DE)  ................................. 101 25 453
May 25, 2001   (DE)  ............................ 201 08 704 U

(51) Int. Cl.
*A61K 7/13* (2006.01)
(52) U.S. Cl. ........................ 8/405; 8/406; 8/410; 8/412; 8/424; 8/570; 8/571; 8/576; 8/577; 548/400; 549/29; 549/200
(58) Field of Classification Search .................... 8/405, 8/406, 410, 412, 424, 570, 571, 576, 577; 548/400; 549/29, 200
See application file for complete search history.

(56) References Cited

U.S. PATENT DOCUMENTS 3,893,803 A    7/1975   Kaiser ........................... 8/10.2

FOREIGN PATENT DOCUMENTS

| DE | CH 558 318 | * | 1/1975 |
|---|---|---|---|
| DE | 30 16 905 A1 | | 11/1981 |
| DE | 32 33 541 A | | 3/1984 |
| DE | 198 59 800 A | | 6/2000 |
| DE | 201 10 355 U | | 10/2001 |
| DE | 201 10 356 U | | 10/2001 |
| EP | 0 904 774 A | | 9/1999 |
| FR | 1 396 684 A | | 4/1965 |
| WO | 99/15148 | | 4/1999 |

OTHER PUBLICATIONS

STIC Search Report filed Mar. 30, 2005.*
STN filed Mar. 29, 2005.*
Attia et al: "Chemical and Biological Reactivity of . . . " Egyption Journal of Chemistry, vol. 38, No. 5, 1995, pp. 543-553.
Pater R., et al: "Photostable O-Hydroxyphenylquinazolines" Journal of Heterocyclic Chemistry, vol. 7, No. 5, 1970, pp. 1113-1124.
Sartori G., et al: "Selective Synthesis of Unsymmetrical Hydrxylated and Methoxylated Biaryls" Journal of Organic Chemistry, vol. 58, 1993, pp. 7271-7273.
Karpel Vel Leitner N., et al: "Kinetics and Mechanics of the Photolytic . . . " Chemosphere, vol. 32, No. 5, 1996, pp. 893-906.
Hogberg H-E et al: "Dibenzofuraus from the Acid-Catalysed Reaction of Alkyl-P-Benzoquinones . . . " Acta Chemica Scandinavica. Series B—Organic Chemistry and Biochemistry, Munksgaad, Copenhagen, DK, No. 33, 1979, pp. 271-276.
Dol. G., et al: "Synthesis of 5-Substituted Resorcinol Derivatives . . . " European Journal of Organic Chemistry, 1998, pp. 359-364.

(Continued)

Primary Examiner—Eisa Elhilo
(74) Attorney, Agent, or Firm—Michael J. Striker

(57) ABSTRACT

1,3-Dihydroxybenzene derivatives of general formula (I) or (Ia) or physiologically tolerated, water-soluble salts thereof

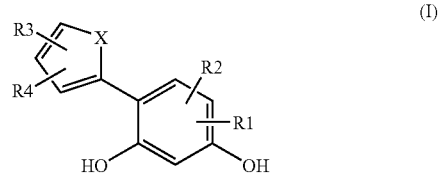

(I)

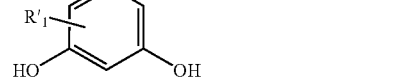

(Ia)

wherein R'1 denotes a substituted pyridyl group, a pyrimidyl group, a group of formula (IIa) or (IIIa)

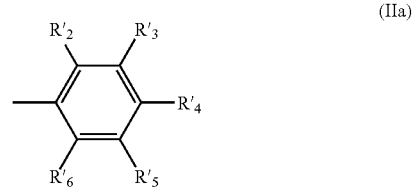

(IIa)

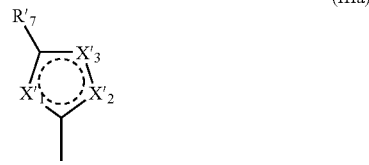

(IIIa)

and the dyeing agents for keratin fibers containing these compounds.

24 Claims, No Drawings

OTHER PUBLICATIONS

Pummerer R., et al: "Die Kondensation Von Chinonen Mit . . . " Chemische Berichte, XX, XX, No. 60, 1927, pp. 1442-1451.

Chandrasekharan V., et al: "Synthesis of 5-Alkyl . . . " Indian Journal of Chemistry, Jodhpur, IN, No. 16B, Nov. 1978, pp. 970-972.

Raistrick H., et al: "Studies in the Biochemistry . . . " The Biochemical Journal, vol. 55, 1953, pp. 421-433.

Erdtman H., et al: "The Synthesis of Unsymmetrical Biphenyl Derivatives by Mixed Ullmann Coupling" Acta Chemica Scandinavica, vol. 15, 1961, pp. 1761-1764.

Nilsson M., et al: "Synthesis of Aucuparin and . . . " Acta Chemica Scandinavica, vol. 75, 1931, pp. 1157-1159.

Devlin J.P.: "6H-Dienzo . . . " Canadian Journal of Chemistry, vol. 53, 1975, pp. 343-349.

Spath E., et al: "Ueber Die Konstitution Des Sappanins" Monatsefte Der Chemie, 1930, pp. 342-351.

Luening U., et al: "Concave Reagents-14 . . . " Tetrahedron Letters, vol. 34, No. 32, pp. 5063-5066.

Astles Peter C., et al: "Selective Endothelin a Receptor . . . " Journal of Medical Chemistry, America Chemical Society, Washington, US, vol. 41, 1998, pp. 2732-2744.

Jaxa-Chmies A., et al: "A New Route to 5-Substituted . . . " Journal of Chemical Society, Perkin Transactions 1, Chemical Society. Letchworth, GB, 1980, pp. 170-175.

"Protective Grou . . . S" in Prganic Synthesis, Second Edition, Chapter 3, Wiley Interscience, 1991, pp. 142-171.

* cited by examiner

1,3-DIHYDROXYBENZENE DERIVATIVES AND COLORANTS CONTAINING SAID COMPOUNDS

BACKGROUND OF THE INVENTION

1. Field of the Invention

The invention relates to novel m-dihydroxybenzene derivatives and to agents for dyeing keratin fibers containing these compounds.

2. Description of the Related Art

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diamino-1-(2-hydroxyethyl)pyrazole, and suitable couplers are, for example, resorcinol, 2-methylresorcinol, 1-naphthol, 3-aminophenol, m-phenylenediamine, 2-amino-4-(2'-hydroxyethyl)aminoanisole, 1,3-diamino-4-(2'-hydroxyethoxy)-benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals, such colorations must remain stable over a period of at least 4 to 6 weeks. Moreover, by combining appropriate developers and couplers, it must be possible to create a wide range of different color shades.

Attempts have already been made to improve the properties of m-dihydroxybenzenes by introduction of substituents. Thus, for example, resorcinols substituted in the 4-position are known from European Unexamined Patent Application EP 0 904 774 and WO Unexamined Patent Application 99/15148. Moreover, German Unexamined Patent Applications DE 30 016 905 and DE 198 59 800 teach the use of substituted m-dihydroxybenzenes in oxidation hair colorants. With the currently known dyeing agents, however, it is not possible to meet the requirements placed on dyeing agents in all respects. Hence, the need continued to exist for novel couplers that would meet the aforesaid requirements to a particularly high degree.

SUMMARY OF THE INVENTION

We have now found that certain 1,3-dihydroxybenzene derivatives of general formula (I) or (Ia) meet the requirements placed on couplers to a particularly high degree and that with most known developers they give strong color shades having unusual color intensity, light fastness and wash fastness.

The object of the present invention is therefore novel 1,3-dihydroxy-4-heteroarylbenzene derivatives of general formula (I) or the physiologically tolerated, water-soluble salts thereof

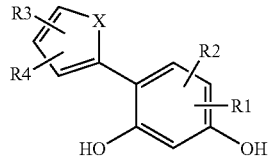

(I)

wherein

X denotes oxygen, sulfur or N—R5;

R1 and R2 can be equal or different and, independently of each other, denote hydrogen, a halogen atom (F, Cl, Br, I), a hydroxyl group, a $C_1$–$C_4$-alkoxy group, a $C_1$–$C_4$-hydroxyalkoxy group, a $C_1$–$C_6$-alkyl group, a $C_1$–$C_4$-alkylthioether group, a trifluoromethyl group, a —Si($CH_3$)$_3$ group, a $C_1$–$C_4$-hydroxyalkyl group or a $C_2$–$C_4$-dihydroxyalkyl group;

R3 and R4 can be equal or different and, independently of each other, denote hydrogen, a hydroxyl group, a halogen atom, a cyano group, a $C_1$–$C_4$-alkoxy group, a $C_1$–$C_6$-alkyl group, a $C_1$–$C_4$-alkylthioether group, a mercapto group, a nitro group, an amino group, a $C_1$–$C_4$-alkylamino group, a di($C_1$–$C_4$)alkylamino group, a —C(O)H group, a —C(O)$CH_3$ group, a —C(O)$CF_3$ group, an —Si($CH_3$)$_3$ group, a $C_1$–$C_4$-hydroxyalkyl group or a $C_2$–$C_4$-dihydroxy-alkyl group; and R5 denotes hydrogen, a $C_1$–$C_6$-alkyl group, a $C_2$–$C_4$-hydroxyalkyl group, a phenyl group or an acetyl group.

Compounds of formula (I) are, for example, the following:

1,3-dihydroxy-4-(thiophen-2-yl)benzene; 1,3-dihydroxy-4-(1-methyl-1H-pyrrol-2-yl)-benzene; 1,3-dihydroxy-4-(pyrrol-2-yl)benzene; 1,3-dihydroxy-4-(furan-2-yl)benzene; 1,3-dihydroxy-4-(3-aminothiophen-2-yl)benzene; 1,3-dihydroxy-4-(3-chlorothiophen-2-yl)benzene; 1,3-dihydroxy-4-(3-methylthiophen-2-yl)-benzene; 1,3-dihydroxy-4-(3-nitrothiophen-2-yl)benzene; 1,3-dihydroxy-4-(4-aminothiophen-2-yl)benzene; 1,3-dihydroxy-4-(4-chlorothiophen-2-yl)benzene; 1,3-dihydroxy-4-(4-methylthiophen-2-yl)benzene; 1,3-dihydroxy-4-(4-nitrothiophen-2-yl)benzene; 1,3-dihydroxy-4-(5-nitro-thiophen-2-yl)benzene; 1,3-dihydroxy-4-(5-aminothiophen-2-yl)benzene; 1,3-dihydroxy-4-(5-chlorothiophen-2-yl)benzene; 1,3-dihydroxy-4-(5-methylthiophen-2-yl)benzene; 1,3,5-trihydroxy-4-(thiophen-2-yl)benzene; 1,2,3-trihydroxy-4-(thiophen-2-yl)benzene; 1,3,6-trihydroxy-4-(thiophen-2-yl)-benzene; 1,3-dihydroxy-2-methyl-4-(thiophen-2-yl)-benzene; 1,3-dihydroxy-5-methyl-4-(thiophen-2-yl)benzene; 1,3-dihydroxy-6-methyl-4-(thiophen-2-yl)benzene; 1,3-dihydroxy-2-chloro-4-(thiophen-2-yl)benzene; 1,3-dihydroxy-5-chloro-4-(thiophen-2-yl)-benzene; 1,3-dihydroxy-6-chloro-4-(thiophen-2-yl)benzene; 1,3-dihydroxy-2-methoxy-4-(thiophen-2-yl)benzene; 1,3-dihydroxy-5-methoxy-4-(thiophen-2-yl)benzene and 1,3-dihydroxy-6-methoxy-4-(thiophen-2-yl)benzene.

Preferred compounds of formula (I) are those wherein (i) one or more of the R1, R2, R3 and R4 groups denote hydrogen and X denotes sulfur or oxygen or (ii) R1 and R2 simultaneously denote hydrogen and X denotes sulfur.

Another object of the invention are 1,3-dihydroxybenzene derivatives of formula (Ia) or the physiologically tolerated, water-soluble salts thereof:

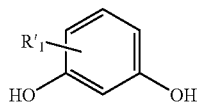

wherein R'1 denotes a substituted pyridyl group, a pyrimidyl group, a group of formula (IIa):

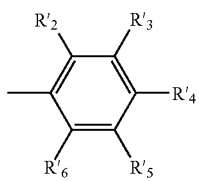

or a group of formula (IIIa):

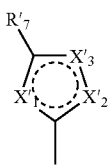

wherein R'2, R'3, R'4, R'5 and R'6, independently of each other, denote hydrogen, a halogen atom (F, Cl, Br, I), a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkylthioether group, a mercapto group, a nitro group, an amino group, a $C_1$–$C_4$-alkylamino group, a hydroxy-($C_1$–$C_4$)alkylamino group, a di($C_1$–$C_4$)-alkylamino group, a di[hydroxy ($C_1$–$C_4$)-alkyl]amino group, a dihydroxy-($C_3$–$C_4$—)-alkylamino group, a [hydroxy-($C_1$–$C_4$)-alkyl]-$C_1$–$C_4$-alkylamino group, a trifluoromethyl group, a —C(O)H group, a —C(O)CH$_3$ group, a —C(O)CF$_3$ group, an —Si(CH$_3$)$_3$ group, a $C_1$–$C_4$-hydroxyalkyl group or a $C_2$–$C_4$-dihydroxyalkyl group, or two adjacent R2 to R6 groups form an —O—CH$_2$—O— bridge;

X'1 denotes sulfur, nitrogen, oxygen, C—R'9 or N—R'8;

X'2 denotes sulfur, nitrogen, oxygen, C—R'10 or N—R'8;

X'3 denotes sulfur, nitrogen, oxygen, C—R'11 or N—R'8;
R'7, R'9, R'10 and R'11, independently of each other, denote hydrogen, a halogen atom, a cyano group, a $C_1$–$C_4$-alkoxy group, a $C_1$–$C_6$-alkyl group, a $C_1$–$C_4$-alkylthioether group, a mercapto group, a nitro group, an amino group, a $C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)CH$_3$ group, a —C(O)CF$_3$ group, an —Si(CH$_3$)$_3$ group, a $C_1$–$C_4$-hydroxyalkyl group or a $C_3$–$C_4$-dihydroxyalkyl group; and R'8 denotes hydrogen, a $C_1$–$C_6$-alkyl group, a $C_2$–$C_4$-hydroxyalkyl group, a phenyl group or an acetyl group, provided that at least one and at the most two of the X'1 to X'3 groups denote C—R'9, C—R'10 or C—R'11 and at the most one of the X'1 to X'3 groups denotes sulfur, oxygen or N—R'8, and R'1 does not stand for a phenyl group or hydroxy-phenyl group.

Compounds of formula (Ia) are, for example:

1,3-dihydroxy-5-(thiophen-2-yl)benzene; 1,3-dihydroxy-5-(1-methyl-1H-pyrrol-2-yl)benzene; 1,3-dihydroxy-5-(pyrrol-2-yl)benzene; 1,3-dihydroxy-5-(furan-2-yl)benzene; 1,3-dihydroxy-5-(3-aminothiophen-2-yl)benzene; 1,3-dihydroxy-5-(3-chlorothiophen-2-yl)benzene; 1,3-dihydroxy-5-(3-methylthiophen-2-yl)-benzene; 1,3-dihydroxy-5-(3-nitrothiophen-2-yl)benzene; 1,3-dihydroxy-5-(4-aminothiophen-2-yl)benzene; 1,3-dihydroxy-5-(4-chlorothiophen-2-yl)benzene; 1,3-dihydroxy-5-(4-methylthiophen-2-yl)benzene; 1,3-dihydroxy-5-(4-nitrothiophen-2-yl)benzene; 1,3-dihydroxy-5-(5-nitrothiophen-2-yl)benzene; 1,3-dihydroxy-5-(5-aminothiophen-2-yl)benzene; 1,3-dihydroxy-5-(5-chlorothiophen-2-yl)benzene; 1,3-dihydroxy-5-(5-methylthiophen-2-yl)benzene; 1,3,5-trihydroxy-5-(thiophen-2-yl)benzene; 1,2,3-trihydroxy-5-(thiophen-2-yl)benzene; 1,3,6-trihydroxy-5-(thiophen-2-yl)benzene; 1,3-dihydroxy-2-methyl-5-(thiophen-2-yl)benzene; 1,3-dihydroxy-5-methyl-5-(thiophen-2-yl)benzene; 1,3-dihydroxy-6-methyl-5-(thiophen-2-yl)benzene; 1,3-dihydroxy-2-chloro-5-(thiophen-2-yl)benzene; 1,3-dihydroxy-5-chloro-5-(thiophen-2-yl)benzene; 1,3-dihydroxy-6-chloro-5-(thiophen-2-yl)benzene; 1,3-dihydroxy-2-methoxy-5-(thiophen-2-yl)benzene; 1,3-dihydroxy-5-methoxy-5-(thiophen-2-yl)benzene; 1,3-dihydroxy-6-methoxy-5-(thiophen-2-yl)benzene; 1,3-dihydroxy-2-(thiophen-2-yl)benzene; 1,3-dihydroxy-2-(1-methyl-1H-pyrrol-2-yl)benzene; 1,3-dihydroxy-2-(pyrrol-2-yl)benzene; 1,3-dihydroxy-2-(furan-2-yl)benzene; 1,3-dihydroxy-2-(3-aminothiophen-2-yl)benzene; 1,3-dihydroxy-2-(3-chloro-thiophen-2-yl)benzene; 1,3-dihydroxy-2-(3-methylthiophen-2-yl)benzene; 1,3-dihydroxy-2-(3-nitrothiophen-2-yl)benzene; 1,3-dihydroxy-2-(4-amino-thiophen-2-yl)benzene; 1,3-dihydroxy-2-(4-chlorothiophen-2-yl)benzene; 1,3-dihydroxy-2-(4-methylthiophen-2-yl)benzene; 1,3-dihydroxy-2-(4-nitrothiophen-2-yl)benzene; 1,3-dihydroxy-2-(5-nitrothiophen-2-yl)benzene; 1,3-dihydroxy-2-(5-aminothiophen-2-yl)benzene; 1,3-dihydroxy-2-(5-chloro-thiophen-2-yl)benzene; 1,3-dihydroxy-2-(5-methyl-thiophen-2-yl)benzene; 1,3,5-trihydroxy-2-(thiophen-2-yl)benzene; 1,2,3-trihydroxy-2-(thiophen-2-yl)benzene; 1,3,6-trihydroxy-2-(thiophen-2-yl)benzene; 1,3-dihydroxy-2-methyl-2-(thiophen-2-yl)-benzene; 1,3-dihydroxy-5-methyl-2-(thiophen-2-yl)benzene; 1,3-di-hydroxy-6-methyl-2-(thiophen-2-yl)benzene; 1,3-dihydroxy-2-chloro-2-(thiophen-2-yl)-benzene; 1,3-dihydroxy-5-chloro-2-(thiophen-2-yl)benzene; 1,3-dihydroxy-6-chloro-2-(thiophen-2-yl)benzene; 1,3-dihydroxy-2-methoxy-2-(thiophen-2-yl)benzene; 1,3-dihydroxy-5-methoxy-2-(thiophen-2-yl)benzene; 1,3-dihydroxy-6-methoxy-2-(thiophen-2-yl)benzene; 1,3-dihydroxy-4-(pyridin-2-yl)benzene; 1,3-dihydroxy-4-(pyrimidin-2-yl)-benzene; 1,3-dihydroxy-4-(5-methylpyridin-2-yl)benzene; 5-(2,4-dihydroxyphenyl)-nicotinonitrile; 1,3-dihydroxy-4-(5-nitropyridin-2-yl)benzene; 1,3-dihydroxy-4-(thiophen-3-yl)-benzene; 4'-methylbiphenyl-2,4-diol; 4'-fluorobiphenyl-2,4-diol; 1,3-dihydroxy-4-(4-methylthiophen-3-yl)benzene; 2',4'-dihydroxybiphenyl-4-carbonitrile; 1,3-dihydroxy-4-(2-chlorothiophen-3-yl)benzene; 1-(2',4'-dihydroxybiphenyl-3-yl)ethanone; 1,3-dihydroxy-4-benzo[1,3]dioxol-5-yl-benzene; 4'-nitrobiphenyl-2,4-diol; 2'-nitrobiphenyl-2,4-diol; 4-(5-nitrothiophen-2-yl)-benzene; 4'-trifluoromethylbiphenyl-2,4-diol; 2',4'-dimethylbiphenyl-2,4-diol; 3'-methoxy-biphenyl-2,4-diol; 4'-chlorobiphenyl-2,4-diol; 1,3-dihydroxy-5-(pyridin-2-yl)benzene; 1,3-dihydroxy-5-(pyrimidin-2-yl)benzene; 1,3-dihydroxy-5-(thiophen-3-yl)-benzene; 5-thiophen-2-yl-benzene; 1,3-dihydroxy-(5-thiazol-2-yl)benzene; 4'-methylbiphenyl-3,5-diol; 1,3-dihydroxy-5-(5-methylpyridin-2-yl)-benzene; 4'-fluorobiphenyl-3,5-diol; 1,3-dihydroxy-5-(4-methyl-thiophen-3-yl)benzene; 3',5'-dihydroxybiphenyl-4-carbonitrile; 1,3-dihydroxy-5-(2-chlorothiophen-3-yl)-benzene; 1-(3',5'-dihydroxybiphenyl-3-yl)ethanone; 4'-nitrobiphenyl-3,5-diol; 2'-nitrobiphenyl-3,5-diol; 4'-trifluoromethylbiphenyl-3,5-diol; 2',4'-dimethylbiphenyl-3,5-diol; 3'-methoxy-biphenyl-3,5-diol; 4'-chlorobiphenyl-3,5-diol; 1,3-dihydroxy-5-(5-nitropyridin-2-yl)benzene; 4'-methylsulfanylbiphenyl-3,5-diol; 2'-chloro-4'-nitrobiphenyl-3,5-diol; 4'-methylsulfanyl-biphenyl-2,4-diol and 1,3-dihydroxy-4-(thiazol-2-yl)benzene, as well as the physiologically tolerated salts thereof.

Preferred compounds of formula (Ia) are those wherein:

(i) X'2 denotes C—R'10 and X'1 denotes sulfur and X'3 denotes C—R'11, or X'1 denotes C—R'9 and X'3 denotes sulfur or (ii) X'2 denotes C—R'10 and X'1 denotes sulfur and X'3 denotes C—R'11 or X'1 denotes C—R'9 and X'3 denotes sulfur, and at least one of the R'9 to R'11 groups denotes hydrogen.

Particularly preferred are the following compounds of formula (I) and (Ia):

1 3-dihydroxy-4-(thiophen-2-yl)benzene; 1,3-dihydroxy-4-(5-nitrothiophen-2-yl)-benzene; 1,3-dihydroxy-4-(3-methylthiophen-2-yl)benzene; 1,3-dihydroxy-4-(furan-2-yl)benzene; 1,3-dihydroxy-5-(5-chlorothiophen-2-yl)benzene; 1,3-dihydroxy-5-(3-methylthiophen-2-yl)benzene; 1,3-dihydroxy-4-(thiophen-3-yl)benzene and 1,3-dihydroxy-5-(thiophen-3-yl)benzene as well as the physiologically tolerated salts thereof.

The 1,3-dihydroxybenzene derivatives of formula (I) and (Ia) can be prepared by known methods of synthesis. The synthesis of the compounds of the invention can be accomplished by palladium(0)-catalyzed coupling (i) of a substituted benzene of formula (II) with a heteroaryl compound of formula (III) or (ii) of a substituted benzene of formula (IIa) with a compound of formula R'1—Rd followed by elimination of the protective group:

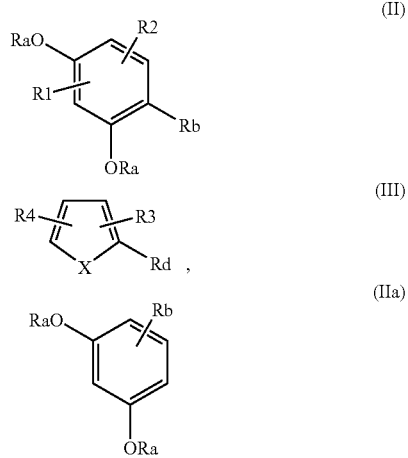

wherein

Rb stands for halogen (F, Cl, Br, I) and Rd denotes $B(OH)_2$, or Rb stands for $B(OH)_2$ and Rd for halogen (F, Cl, Br, I);

Ra denotes a protective group as described, for example, in the chapter on "Protective Groups", in Organic Synthesis, chapter 3, Wiley Interscience, 1991, and X, R1, R2, R3, R4 and R'1 have the same meaning as in formula (I) and (Ia).

The 1,3-dihydroxybenzene derivatives of formula (I) and (Ia) are highly water-soluble and give colorations of excellent color intensity and color stability, particularly in terms of light fastness, wash fastness and rubbing fastness. They also have excellent storage stability, particularly as constituents of the oxidation colorants described in the following.

Another object of the present invention are therefore agents for oxidative dyeing of keratin fibers, for example hair, furs, feathers or wool, particularly human hair, based on a developer-coupler combination containing at least one 1,3-dihydroxybenzene derivative of formula (I) or (Ia), and wherein in formula (Ia) R'1 can, in addition to the meanings given in the foregoing, also denote a phenyl group or hydroxyphenyl group.

The compounds of formula (I) and (Ia) can be used as the free phenols as well as in the form of their physiologically tolerated salts with inorganic or organic bases, for example, sodium hydroxide, potassium hydroxide, sodium carbonate or tetrabutylammonium hydroxide.

The 1,3-dihydroxybenzene derivatives of formula (I) and/or (Ia) are present in the colorants of the invention in a total amount of about 0.005 to 20 wt. %, an amount of about 0.01 to 5.0 wt. % and particularly 0.1 to 2.5 wt. % being preferred.

Suitable developers are, for example, 1,4-diaminobenzene (p-phenylenediamine); 1,4-diamino-2-methylbenzene (p-toluylene-diamine); 1,4-diamino-2,6-dimethylbenzene; 1,4-diamino-3,5-diethyl-benzene; 1,4-diamino-2,5-dimethylbenzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl)benzene; 2,5-diaminobiphenyl; 1,4-diamino-2-methoxymethylbenzene; 1,4-diamino-2-aminomethylbenzene; 1,4-diamino-2-hydroxymethylbenzene; 1,4-diamino-2-(2-hydroxyethoxy)benzene; 2-[2-(acetylamino)ethoxy]-1,4-diaminobenzene; 4-phenylaminoaniline; 4-dimethylaminoaniline; 4-diethylaminoaniline; 4-dipropyl-aminoaniline; 4-[ethyl-(2-hydroxyethyl)amino]aniline; 4-[di(2-hydroxyethyl)-amino]aniline; 4-[di (2-hydroxyethyl)amino]-2-methylaniline; 4-[(2-methoxyethyl)-amino]aniline; 4-[(3-hydroxypropyl)amino]aniline; 4-[(2,3-dihydroxypropyl)-amino]aniline; 1,4-diamino-2-(1-hydroxyethyl)benzene; 1,4-diamino-2-(2-hydroxyethyl)benzene; 1,4-diamino-2-(1-methylethyl)benzene; 1,3-bis-[(4-aminophenyl)-(2-hydroxyethyl)amino]-2-propanol; 1,4-bis-[(4-aminophenyl)-amino]butane; 1,8-bis(2,5-diaminophenoxy)-3,6-dioxaoctane; 4-aminophenol; 4-amino-3-methylphenol; 4-amino-3-(hydroxymethyl)phenol; 4-amino-3-fluoro-phenol; 4-methylaminophenol; 4-amino-2-(aminomethyl)phenol; 4-amino-2-(hydroxymethyl)phenol; 4-amino-2-fluorophenol; 4-amino-2-[(2-hydroxyethyl)-amino]-methylphenol; 4-amino-2-methylphenol; 4-amino-2-(methoxymethyl)-phenol; 4-amino-2-(2-hydroxyethyl)phenol; 5-aminosalicylic acid; 2,5-diamino-pyridine; 2,4,5,6-tetramino-pyrimidine; 2,5,6-triamino-4-(1H)-pyrimidone; 4,5-diamino-1-(2-hydroxyethyl)-1H-pyrazole; 4,5-diamino-1-(1- methylethyl)-1H-pyrazole; 4,5-diamino-1-[(4-methylphenyl)methyl]-1H-pyrazole; 1-[(4-chloro-phenyl)-methyl]-4,5-diamino-1H-pyrazole; 4,5-diamino-1-methyl-1H-pyrazole; 2-aminophenol; 2-amino-6-methylphenol; 2-amino-5-methylphenol and 1,2,4-trihydroxybenzene.

In addition to the compounds of formula (I) and/or (Ia), the colorant of the invention can also contain other known couplers, for example N-(3-dimethylaminophenyl)urea; 2,6-diaminopyridine; 2-amino-4-[(2-hydroxy-ethyl)-amino]anisole; 2,4-diamino-1-fluoro-5-methylbenzene; 2,4-diamino-1-methoxy-5-methyl-benzene; 2,4-diamino-1-ethoxy-5-methylbenzene; 2,4-diamino-1-(2-hydroxyethoxy-5-methylbenzene; 2,4-di[(2-hydroxyethyl)amino]-1,5-dimethoxybenzene; 2,3-diamino-6-methoxypyridine; 3-amino-6-methoxy-2-(methylamino)pyridine; 2,6-diamino-3,5-dimethoxypyridine; 3,5-diamino-2,6-dimethoxypyridine; 1,3-diaminobenzene; 2,4-diamino-1-(2-hydroxyethoxy)-benzene; 1,3-diamino-4-(2,3-dihydroxypropoxy)benzene; 1,3-diamino-4-(3-hydroxypropoxy)benzene; 1,3-diamino-4-(2-methoxyethoxy)-benzene; 2,4-diamino-1,5-di(2-hydroxyethoxy)benzene; 1-(2-aminoethoxy)-2,4-diaminobenzene; 2-amino-1-(2-hydroxyethoxy)-4-methylaminobenzene; 2,4-diamino-phenoxy acetic acid; 3-[di(2-hydroxyethyl)amino]aniline; 4-amino-2-di[(2-hydroxyethyl)amino]-1-ethoxybenzene; 5-methyl-2-(1-methylethyl)phenol; 3-[(2-hydroxyethyl)amino]aniline; 3-[(2-aminoethyl)-amino]aniline; 1,3-di(2,4-diaminophenoxy)propane; di(2,4-diaminophenoxy)methane; 1,3-diamino-2,4-dimethoxybenzene; 2,6-bis(2-hydroxyethyl)aminotoluene; 4-hydroxyindole; 3-dimethylaminophenol; 3-diethylaminophenol; 5-amino-2-methyl-phenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxyphenyl)amino]acetamide; 5-[(2-hydroxyethyl)-amino]-4-methoxy-2-methyl-phenol; 5-[(2-hydroxyethyl)amino]-2-methylphenol; 3-[(2-hydroxyethyl)amino]phenol; 3-[(2-methoxyethyl)amino]phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxy-pyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; 1,2-di-chloro-3,5-dihydroxy-4-methylbenzene; 1,5-dichloro-2,4-dihydroxybenzene; 1,3-di-hydroxy-2-methylbenzene; 3,4-methylene-dioxyphenol; 3,4-methylenedioxyaniline; 5-[(2-hydroxyethyl)amino]-1,3-benzodioxole; 6-bromo-1-hydroxy-3,4-methylenedioxybenzene; 3,4-diamino-benzoic acid; 3,4-dihydro-6-hydroxy-1,4-(2H)-benzoxazine; 6-amino-3,4-dihydro-1,4[2H]benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

The couplers and developers can be present in the colorant of the invention either individually or in admixture with one another, the total amount of each of the couplers and developers in the colorant of the invention being about 0.005 to 20 wt. %, preferably about 0.01 to 5 wt. % and particularly 0.1 to 2.5 wt. % (based on the total amount of colorant).

The total amount of the developer-coupler combination contained in the colorant described herein is preferably about 0.01 to 20 wt. %, an amount of about 0.02 to 10 wt. % and especially 0.2 to 6 wt. % being particularly preferred. In general, the developers and couplers are used in approximately equimolar amounts. In this respect, it is not disadvantageous, however, if the developers are present in a certain excess or deficiency.

Moreover, the colorants of the invention can also contain other dye components, for example 6-amino-2-methylphenol and 2-amino-5-methylphenol, as well as common direct dyes from the group of acid or basic dyes, triphenylmethane dyes, aromatic nitro dyes, azo dyes and disperse dyes. The colorants of the invention can contain these dye components in an amount from about 0.1 to 4 wt. %.

The additional couplers and developers and the other dye components, provided they are bases, can of course also be used in the form of their physiologically tolerated salts with organic or inorganic acids, for example hydrochloric acid or sulfuric acid, or—if they contain aromatic OH groups—in the form of their salts with bases, for example Moreover, if the colorants of the invention are to be used for coloring hair, they can also contain other common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example, solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active substances, for example fatty alcohol sulfates, ethoxylated fatty alcohol sulfates, alkylsulfonates, alkylbenzenesulfonates, alkyltrimethyl-ammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The constituents are used in amounts commonly employed for such purposes, for example the wetting agents and emulsifiers at a concentration of about 0.5 to 30 wt. %, the thickeners in an amount from about 0.1 to 30 wt. % and the hair-care agents at a concentration from about 0.1 to 5 wt. %.

Depending on the composition, the colorant of the invention can be weakly acidic, neutral or alkaline. In particular, it has a pH of 6.5 to 11.5. Adjustment to a basic pH is preferably done with ammonia, but it can also be done with an organic amine, for example monoethanolamine and triethanolamine, or with an inorganic base, such as sodium hydroxide and potassium hydroxide. Suitable for adjustment to an acidic pH are inorganic or organic acids, for example phosphoric acid, acetic acid, citric acid or tartaric acid.

For oxidative dyeing of hair, the afore-described colorant is mixed with an oxidant just before use, and the resulting mixture is applied to hair in an amount sufficient for the hair-dyeing treatment, in general about 60 to 200 grams, depending on the hair fullness.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when stronger bleaching of the hair is wanted at the same time. The mixture is allowed to act on the hair at 15 to 50° C. for about 10 to 45 mm, preferably 30 mm, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a 1,3-dihydroxybenzene derivative of formula (I) and/or (Ia) as coupler give hair colorations of excellent color stability, particularly in terms of light fastness, wash fastness and rubbing fastness. As far as their dyeing properties are concerned, the hair colorants of the invention provide a wide range of different color shades from blond to brown, purple, violet and even blue and black, depending on the kind and composition of the dye components. The color shades are noteworthy for their unusual color intensity. The very good coloring properties of the hair colorant of the present patent application also manifest themselves in that this colorant makes it possible to dye gray hair, previously not damaged chemically, without any problems and with good covering power.

The following examples illustrate the object of the invention in greater detail without limiting its scope.

EXAMPLES

Example 1

Synthesis of 1,3-dihydroxybenzenes (General Method of Synthesis)

A. Synthesis of 2-[2-bromo-5-(tetrahydro-2H-pyran-2-yloxy)phenoxy]tetrahydro-2H-pyran To a solution of 9.5 g (40 mmol) of 4-bromo-1,3-dihydroxybenzene and 5 g (20 mmol) of toluene-4-sulfonic acid pyridine salt in 50 mL of dichloromethane was added dropwise 9-g (105 mmol) of 3,4-dihydro-2H-pyran under argon. The reaction mixture was allowed to agitate 18 hours. The reaction mixture was then poured into 100 mL of ethyl acetate and the organic phase was extracted with dilute sodium hydroxide and then dried with magnesium sulfate. The solvent was distilled off in a rotary evaporator, and the residue was purified on silica gel with petroleum ether/ethyl acetate (7:1).

This gave 9.5 g (54% of the theoretical) of 2-[2-bromo-5-(tetrahydro-2H-pyran-2-yloxy)phenoxy]tetrahydro-2H-pyran.

B. Synthesis of 2-{2-(4,4,5,5-tetramethyl[1,3,2]dioxoborolan-2-yl)-5-(tetrahydro-2H-pyran-2-yloxy)phenoxy}tetrahydro-2H-pyran 210 mL of degassed dioxan was added under argon to a mixture of 5.5 g (154 mmol) of 2-[2-bromo-5-(tetrahydro-2H-pyran-2-yloxy)phenoxy]tetrahydro-2H-pyran from step A, 9 g (355 mmol) of 4,4,5,5,4',4',5',5'-octamethyl[2,2']-bi{[1,3,2]dioxaborinanyl}, 1.5 g (2.2 mmol) of dichloro-[1,1'-bis(diphenyl-phosphino)ferrocene]palladium [PdCl$_2$(dppf)] and 6.2 g (63.2 mmol) of potassium acetate. The mixture was allowed to agitate at 80° C. for 24 hours and was then poured into water and extracted with ethyl acetate. The organic phase was washed with a saturated aqueous solution of sodium chloride, dried over sodium sulfate and then filtered and evaporated. The resulting crude product was purified on deactivated silica gel using a gradient of hexane (100%) and hexane/ethyl acetate (9:1 to 3:2).

This gave 4.70 g (77% of the theoretical) of 2-{2-(4,4,5,5-tetramethyl-[1,3,2]dioxoborolan-2-yl)-5-(tetrahydro-2H-pyran-2-yloxy)phenoxy}tetrahydro-2H-pyran.

C. Synthesis of 1,3-dihydroxybenzenes of formula (I)

0.09 g (0.2 mmol) of 2-{2-(4,4,5,5-tetramethyl[1,3,2]dioxoborolan-2-yl)-5-(tetrahydro-2H-pyran-2-yloxy)phenoxy}tetrahydro-2H-pyran from step B and 0.04 mmol of the appropriate bromo derivative were dissolved in 10 mL of 1,2-dimethoxyethane under argon. Then, 0.01 g (0.005 mmol) of tetrakis(triphenyl-phosphine)palladium and 0.26 mL of 2N potassium carbonate solution were added, and the reaction mixture was heated to 80° C. At the end of the reaction, the reaction mixture was poured into 10 mL of ethyl acetate, and the organic phase was extracted with dilute sodium hydroxide solution and then dried with magnesium sulfate. The solvent was distilled off in a rotary evaporator, and the residue was purified on silica gel with petroleum ether/ethyl acetate (9:1).

a. 1,3-Dihydroxy-4-(thiophen-2-yl)benzene
   Bromo derivative used: 2-bromothiophene
   Mass spectrum: MH+ 192 (100)

b. 1,3-Dihydroxy-4-(5-nitrothiophen-2-yl)benzene
   Bromo derivative used: 2-bromo-5-nitrothiophene
   Mass spectrum: MH+ 237 (100)

c. 1,3-Dihydroxy-4-(3-methylthiophen-2-yl)benzene
   Bromo derivative used: 2-bromo-3-methylthiophene
   Mass spectrum: MH+ 206 (100)

d. 1,3-Dihydroxy-4-(pyridin-2-yl)benzene hydrochloride
   Bromo derivative used: 2-bromopyridine
   Mass spectrum: MH+ 188 (100)

e. 1,3-Dihydroxy-4-(pyrimidin-2-yl)benzene hydrochloride
   Bromo derivative used: 2-bromopyrimidine
   Mass spectrum: MH+ 189 (100)

f. 1,3-Dihydroxy-4-(5-methylpyridin-2-yl)benzene hydrochloride
   Bromo derivative used: 2-bromo-5-methylpyridine
   Mass spectrum: MH+ 188 (100)

g. 5-(2,4-Dihydroxyphenyl)nicotinonitrile hydrochloride
   Bromo derivative used: 3-bromo-5-methylpyridine
   Mass spectrum: MH+ 213 (100)

h. 1,3-Dihydroxy-4-(5-nitropyridin-2-yl)benzene hydrochloride
   Bromo derivative used: 2-bromo-5-nitropyridine
   Mass spectrum: MH+ 233 (100)

i. 1,3-Dihydroxy-4-(thiophen-3-yl)benzene
   Bromo derivative used: 3-bromothiophene
   Mass spectrum: MH+ 193 (100)

j. 4'-Methylbiphenyl-2,4-diol
   Bromo derivative used: 4-bromotoluene
   Mass spectrum: MH+ 201 (100)

k. Biphenyl-2,4,4'-triol
   Bromo derivative used: 4-bromophenol
   Mass spectrum: MH+ 203 (100)

l. Biphenyl-2,4,3'-triol
   Bromo derivative used: 3-bromophenol
   Mass spectrum: MH+ 203 (100)

m. 4'-Fluorobiphenyl-2,4-diol
   Bromo derivative used: 4-bromofluorobenzene
   Mass spectrum: MH+ 205 (100)

n. 1,3-Dihydroxy-4-(4-methylthiophen-3-yl)benzene
   Bromo derivative used: 3-bromo-4-methylthiophene
   Mass spectrum: MH+ 207 (100)

o. 2',4'-Dihydroxybiphenyl-4-carbonitrile
   Bromo derivative used: 4-bromobenzonitrile
   Mass spectrum: MH+ 206 (100)

p. 1,3-Dihydroxy-4-(2-chlorothiophen-3-yl)benzene
   Bromo derivative used: 3-bromo-2-chlorothiophene
   Mass spectrum: MH+ 227 (100)

q. 1-(2',4'-Dihydroxybiphenyl-3-yl)ethanone
   Bromo derivative used: 5-bromoacetophenone
   Mass spectrum: MH+ 229 (100)

r. 1,3-Dihydroxy-4-(benzo[1,3]dioxol-5-yl)benzene
   Bromo derivative used: 5-bromo-1,3-methylenedioxybenzene
   Mass spectrum: MH+ 231 (100)

s. 4'-Nitrobiphenyl-2,4-diol
   Bromo derivative used: 4-bromonitrobenzene
   Mass spectrum: MH+ 232 (100)

t. 2'-Nitrobiphenyl-2,4-diol
   Bromo derivative used: 2-bromonitrobenzene
   Mass spectrum: MH+ 232 (100)

u. 4'-Trifluoromethylbiphenyl-2,4-diol
   Bromo derivative used: 4-bromotrifluorotoluene
   Mass spectrum: MH+ 255 (100)

v. 2',4'-Dimethylbiphenyl-2,4-diol
   Bromo derivative used: 2-bromo-5-methyltoluene
   Mass spectrum: MH+ 215 (100)

w. 3'-Methoxybiphenyl-2,4-diol
   Bromo derivative used: 5-bromoanisole
   Mass spectrum: MH+ 217 (100)

x. 4'-Chlorobiphenyl-2,4-diol
   Bromo derivative used: 4-bromochlorobenzene
   Mass spectrum: MH+ 221 (100)

y. 4'-Methylsulfanylbiphenyl-2,4-diol
   Bromo derivative used: 4-methylsulfanylbromobenzene
   Mass spectrum: MH+ 233 (100)

z. 1,3-Dihydroxy-4-(thiazol-2-yl)benzene
   Bromo derivative used: 2-bromothiazole
   Mass spectrum: MH+ 94 (100)

Example 2

Synthesis of 1,3-dihydroxybenzenes

The synthesis was accomplished by the method given in step C, Example 1.

a. 1,3-Dihydroxy-5-(pyridin-2-yl)benzene hydrochloride
   Bromo derivative used: 3-bromopyridine
   Mass spectrum: MH+ 188 (100)

b. 1,3-Dihydroxy-5-(pyrimidin-2-yl)benzene hydrochloride
   Bromo derivative used: 2-bromopyrimidine
   Mass spectrum: MH+ 189 (100)

c. 1,3-Dihydroxy-5-(thiophen-3-yl)benzene
   Bromo derivative used: 3-bromothiophene
   Mass spectrum: MH+ 193 (100)

d. 1,3-Dihydroxy-5-(thiophen-2-yl)benzene
   Bromo derivative used: 2-bromothiophene
   Mass spectrum: MH+ 192 (100)

e. 1,3-Dihydroxy-5-(thiazol-2-yl)benzene
   Bromo derivative used: 2-bromothiazole
   Mass spectrum: MH+ 94 (100)

f. 4'-Methylbiphenyl-2,4-diol
   Bromo derivative used: 4-bromotoluene
   Mass spectrum: MH+ 201 (100)

g. 1,3-Dihydroxy-4-(5-methylpyridin-2-yl)benzene hydrochloride
   Bromo derivative used: 2-bromo-5-methylpyridine
   Mass spectrum: MH+ 188 (100)

h. Biphenyl-3,5,4'-triol
   Bromo derivative used: 4-bromophenol
   Mass spectrum: MH+ 203 (100)

i. Biphenyl-3,5,3'-triol
   Bromo derivative used: 3-bromophenol
   Mass spectrum: MH+ 203 (100)

j. 4'-Fluorobiphenyl-3,5-diol
   Bromo derivative used: 4-bromofluorobenzene
   Mass spectrum: MH+ 205 (100)

k. 1,3-Dihydroxy-5-(3-methylthiophen-2-yl)benzene
   Bromo derivative used: 2-bromo-3-methylthiophene
   Mass spectrum: MH+ 206 (100)

l. 1,3-Dihydroxy-5-(4-methylthiophen-3-yl)benzene
   Bromo derivative used: 3-bromo-4-methylthiophene
   Mass spectrum: MH+ 207 (100)

m. 3',5'-Dihydroxybiphenyl-4-carbonitrile
   Bromo derivative used: 4-bromobenzonitrile
   Mass spectrum: MH+ 206 (100)

n. 1,3-Dihydroxy-5-(2-chlorothiophen-3-yl)benzene
   Bromo derivative used: 3-bromo-2-chlorothiophene
   Mass spectrum: MH+ 227 (100)

o. 1-(2',4'-Dihydroxybiphenyl-3-yl)ethanone
   Bromo derivative used: 3-bromoacetophenone
   Mass spectrum: MH+ 229 (100)

p. 1,3-Dihydroxy-4-(benzo[1,3]dioxol-5-yl)benzene
   Bromo derivative used: 5-bromo-1,3-methylenedioxybenzene
   Mass spectrum: MH+ 231 (100)

q. 4'-Nitrobiphenyl-2,4-diol
   Bromo derivative used: 4-bromonitrobenzene
   Mass spectrum: MH+ 232 (100)

r. 2'-Nitrobiphenyl-2,4-diol
   Bromo derivative used: 2-bromonitrobenzene
   Mass spectrum: MH+ 232 (100)

s. 1,3-Dihydroxy-5-(5-nitrothiophen-2-yl)benzene
   Bromo derivative used: 2-bromo-5-nitrothiophene
   Mass spectrum: MH+ 237 (100)

t. 4'-Trifluoromethylbiphenyl-3,5-diol
   Bromo derivative used: 4-bromotrifluorotoluene
   Mass spectrum: MH+ 255 (100)

u. 2',4'-Dimethylbiphenyl-3,5-diol
   Bromo derivative used: 2-bromo-5-methyltoluene
   Mass spectrum: MH+ 215 (100)

v. 3'-Methoxybiphenyl-2,4-diol
   Bromo derivative used: 5-bromoanisole
   Mass spectrum: MH+ 217 (100)

w. 4'-Chlorobiphenyl-2,4-diol
   Bromo derivative used: 4-bromochlorobenzene
   Mass spectrum: MH+ 221 (100)

x. 4'-Methylsulfanylbiphenyl-2,4-diol
   Bromo derivative used: 4-methylsulfanylbromobenzene
   Mass spectrum: MH+ 233 (100)

y. 2'-Chloro-4'-nitrobiphenyl-3,5-diol
   Bromo derivative used: 4-bromo-3-chloronitrobenzene
   Mass spectrum: MH+ 266 (100)

Examples 3 to 53

Hair Colorants

Hair colorant solutions having the following composition were prepared:

| | | |
|---|---|---|
| 1.25 mmol | of coupler of formula (I)/(Ia) as per Table 1 |
| 1.25 mmol | of developer as per Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Just before use, 50 g of the foregoing coloring solution was mixed with 50 g of a 6% aqueous hydrogen peroxide solution. The mixture was then applied to bleached hair. After an exposure time of 30 mm at 40° C., the hair was rinsed with water, washed with a commercial shampoo and dried. The resulting color shades are presented in Table 1.

TABLE 1

| Example No. | Coupler of formula (I)/(Ia) | I. 1,4-Diamino-benzene | II. 2,5-Diamino-toluene sulfate | III. 2,5-Diamino-phenyl-ethanol sulfate | IV. 4,5-Diamino-1-(2'-hydroxyethyl)pyrazole sulfate |
|---|---|---|---|---|---|
| 3 | As per Ex. 1a | dark brown | dark brown | dark brown | purple |
| 4 | As per Ex. 1b | brown | medium blond | medium blond | purple |
| 5 | As per Ex. 1c | brown | medium blond | medium blond | purple |
| 6 | As per Ex. 1d | medium blond | bright blond | bright blond | bright purple |
| 7 | As per Ex. 1e | medium blond | bright blond | bright blond | bright purple |
| 8 | As per Ex. 1f | medium blond | bright blond | bright blond | bright purple |
| 9 | As per Ex. 1g | medium blond | bright blond | bright blond | bright purple |
| 10 | As per Ex. 1h | medium blond | bright blond | bright blond | bright purple |
| 11 | As per Ex. 1i | medium blond | blond | blond | bright purple |
| 12 | As per Ex. 1j | medium blond | bright blond | bright blond | bright purple |
| 13 | As per Ex. 1k | medium blond | bright blond | bright blond | bright purple |
| 14 | As per Ex. 1l | brown purple | bright brown-purple | bright brown-purple | purple |
| 15 | As per Ex. 1m | medium blond | bright blond | bright blond | bright purple |
| 16 | As per Ex. 1n | medium blond | bright blond | bright blond | bright purple |
| 17 | As per Ex. 1o | medium blond | bright blond | bright blond | bright purple |
| 18 | As per Ex. 1p | medium blond | bright blond | bright blond | bright purple |
| 19 | As per Ex. 1q | medium blond | bright blond | bright blond | bright purple |
| 20 | As per Ex. 1r | medium blond | bright blond | bright blond | bright purple |
| 21 | As per Ex. 1s | medium blond | blond | blond | bright purple |
| 22 | As per Ex. 1t | medium blond | bright blond | bright blond | bright purple |
| 23 | As per Ex. 1u | medium blond | bright blond | bright blond | bright purple |
| 24 | As per Ex. 1v | medium blond | bright blond | bright blond | bright purple |
| 25 | As per Ex. 1w | medium blond | bright blond | bright blond | bright purple |
| 26 | As per Ex. 1x | medium blond | bright blond | bright blond | bright purple |
| 27 | As per Ex. 1y | medium blond | bright blond | bright blond | bright purple |
| 28 | As per Ex. 1z | gray | bright blue | bright blue | violet |
| 29 | As per Ex. 2a | blond | bright blond | bright blond | bright orange |
| 30 | As per Ex. 2b | blond | bright blond | bright blond | bright orange |
| 31 | As per Ex. 2c | blond | bright blond | bright blond | bright orange |
| 32 | As per Ex. 2d | blond | bright blond | bright blond | bright orange |
| 33 | As per Ex. 2e | blond | bright blond | bright blond | bright orange |
| 34 | As per Ex. 2f | blond | bright blond | bright blond | bright orange |
| 35 | As per Ex. 2g | blond | bright blond | bright blond | bright orange |
| 36 | As per Ex. 2h | blond | bright blond | bright blond | bright orange |
| 37 | As per Ex. 2i | blond | bright blond | bright blond | bright orange |

TABLE 1-continued

| Example No. | Coupler of formula (I)/(Ia) | I. 1,4-Di-amino-benzene | II. 2,5-Diamino-toluene sulfate | III. 2,5-Diamino-phenyl-ethanol sulfate | IV. 4,5-Diamino-1-(2'-hydroxyeth-yl)pyrazole sulfate |
|---|---|---|---|---|---|
| 38 | As per Ex. 2j | blond | bright blond | bright blond | bright orange |
| 39 | As per Ex. 2k | blond | bright blond | bright blond | bright orange |
| 40 | As per Ex. 2l | blond | bright blond | bright blond | bright orange |
| 41 | As per Ex. 2m | blond | bright blond | bright blond | bright orange |
| 42 | As per Ex. 2n | blond | bright blond | bright blond | bright orange |
| 43 | As per Ex. 2o | blond | bright blond | bright blond | bright orange |
| 44 | As per Ex. 2p | blond | bright blond | bright blond | bright orange |
| 45 | As per Ex. 2q | blond | bright blond | bright blond | bright orange |
| 46 | As per Ex. 2r | blond | bright blond | bright blond | bright orange |
| 47 | As per Ex. 2s | blond | bright blond | bright blond | bright orange |
| 48 | As per Ex. 2t | blond | bright blond | bright blond | bright orange |
| 49 | As per Ex. 2u | blond | bright blond | bright blond | bright orange |
| 50 | As per Ex. 2v | blond | bright blond | bright blond | bright orange |
| 51 | As per Ex. 2w | blond | bright blond | bright blond | bright orange |
| 52 | As per Ex. 2x | blond | bright blond | bright blond | bright orange |
| 53 | As per Ex. 2y | blond | bright blond | bright blond | bright orange |

Examples 54 to 63

Hair Colorants

Hair colorant solutions of the following composition were prepared:

| X g | of 1,3-dihydroxy-5-(thiophenyl-2-yl)benzene (coupler K1) [sic - Tr.] |
|---|---|
| U g | of developer E8 to E15 as per Table 2 |
| Y g | of coupler K11 to K33 as per Table 3 |
| Z g | of direct dye D2 or D3 as per Table 4 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair.

After an exposure time of 30 mm at 40° C., the hair was rinsed with water, washed with a commercial shampoo and dried. Table 5 shows the coloring results.

TABLE 2

| Developers | |
|---|---|
| E8 | 1,4-diaminobenzene |
| E9 | 2,5-diaminophenylethanol sulfate |
| E10 | 3-methyl-4-aminophenyl |
| E11 | 4-amino-2-aminomethylphenol dihydrochloride |
| E12 | 4-aminophenol |
| E13 | N,N-bis(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| Couplers | |
|---|---|
| K1 | 1,3-dihydroxy-5-(thiophenyl-2-yl)benzene [sic - Translator] |
| K2 | 1,3-dihydroxy-4-(thiophenyl-2-yl)benzene [sic - Translator] |
| K12 | 2-amino-4-(2'-hydroxyethyl)aminoanisole sulfate |
| K13 | 1,3-diamino-4-(2'-hydroxyethoxy)benzene sulfate |
| K18 | N-(3-dimethylamino)phenylurea |
| K19 | 1,3-bis(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |

TABLE 4

| Direct Dyes | |
|---|---|
| D2 | 6-chloro-2-ethylamino-4-nitrophenol |
| D3 | 2-amino-6-chloro-4-nitrophenol |

TABLE 5

Hair Colorants

| Example No. | 54 | 55 | 56 | 57 | 58 | 59 |
|---|---|---|---|---|---|---|
| Dyes | (Quantity of dye in grams) | | | | | |
| K1 | 0.10 | 0.10 | 0.13 | 0.15 | 0.20 | 0.10 |
| E8 | 0.30 | | | | | |
| E9 | | | | | 0.25 | 0.30 |
| E15 | | 0.25 | 0.30 | 0.25 | | |
| K12 | | | 0.16 | | | |
| K12 [sic - Transl.] | | | 0.16 | | | |
| K13 | 0.05 | | | | 0.15 | 0.15 |
| K18 | | 0.10 | | | | |
| K19 | | | | 0.15 | | |
| K13 [sic] | 0.05 | 0.10 | | 0.15 | 0.15 | 0.15 |
| K31 | | | | 0.05 | | |
| K32 | | 0.05 | | | | |
| K33 | | | 0.10 | | | |
| K21 | 0.05 | | | | | |
| K22 | | 0.05 | | | | |
| K23 | | | 0.05 | 0.10 | 0.10 | 0.10 |
| Dyeing result | blond | blond | blond | blond | blond | blond |

| Example No. | 60 | 61 | 62 | 63 |
|---|---|---|---|---|
| Dyes | (Quantity of dye in grams) | | | |
| K1 | 0.20 | 0.20 | 0.20 | 0.20 |
| E8 | 0.15 | | 0.20 | |
| E15 | | 0.20 | | 0.18 |
| E10 | 0.30 | | | |

TABLE 5-continued

Hair Colorants

| | | | | |
|---|---|---|---|---|
| E11 | 0.30 | | | |
| E12 | | 0.30 | | |
| E14 | | | | 0.30 |
| K25 | 0.30 | 0.30 | | 0.30 |
| K26 | | | 0.35 | |
| Dyeing result | red-brown | red-brown | red-brown | red-brown |

Examples 64 to 69

Hair Colorants

Hair colorant solutions of the following composition were prepared:

| | |
|---|---|
| X g | of 1,3-dihydroxy-5-(thiophenyl-2-yl)benzene (coupler K1) [sic - Tr.] |
| U g | of developer E8 o E15 as per Table 2 |
| Y g | of coupler K11 to K33 as per Table 3 |
| Z g | of direct dye D2 or D3 as per Table 4 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 mm at 40° C., the hair was rinsed with water, washed with a commercial shampoo and dried. Table 6 shows the coloring results.

TABLE 6

Hair Colorants

| Example No. Dyes | 64 | 65 | 66 | 67 | 68 | 69 |
|---|---|---|---|---|---|---|
| | (Quantity of dye in grams) | | | | | |
| K1 | 1.10 | 1.10 | 0.60 | 0.20 | 0.40 | 0.40 |
| E8 | 1.50 | | | | | |
| E13 | | 1.60 | | | | 0.70 |
| E15 | | | 1.80 | 0.70 | 0.70 | |
| K12 | 0.60 | | | | | |
| K13 | 0.70 | 1.50 | 1.25 | 0.18 | 0.18 | 0.18 |
| K23 | | | 0.05 | 0.10 | 0.10 | 0.10 |
| K31 | | | 0.60 | 0.20 | | |
| D3 | | | | 0.10 | | |
| D2 | | | | | 0.10 | 0.10 |
| Dyeing result | black | black | black | brown | brown | brown |

Examples 70 to 79

Hair Colorants

Hair colorant solutions of the following composition were prepared:

| | |
|---|---|
| X g | of 1,3-dihydroxy-4-(thiophen-2-yl)benzene (coupler K2) |
| U g | of developer E8 o E15 as per Table 2 |
| Y g | of coupler K11 to K33 as per Table 3 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 mm at 40° C., the hair was rinsed with water, washed with a commercial shampoo and dried. Table 7 shows the coloring results.

TABLE 7

Hair Colorants

| Example No. Dyes | 70 | 71 | 72 | 73 | 74 | 75 |
|---|---|---|---|---|---|---|
| | (Quantity of dye in grams) | | | | | |
| K2 | 0.10 | 0.10 | 0.13 | 0.15 | 0.20 | 0.10 |
| E8 | 0.30 | | | | | |
| E9 | | | | | 0.25 | 0.30 |
| E15 | | 0.25 | 0.30 | 0.25 | | |
| K12 | | | 0.16 | | | |
| K13 | 0.05 | | | | 0.15 | 0.15 |
| K18 | | 0.10 | | | | |
| K19 | | | | 0.15 | | |
| K21 | 0.05 | | | | | |
| K22 | | 0.05 | | | | |
| K23 | | | 0.05 | | 0.10 | 0.10 |
| K24 | | | | 0.10 | | |
| K31 | | | | 0.05 | | |
| K32 | | 0.05 | | | | |
| K33 | | | 0.10 | | | |
| Dyeing result | blond | blond | blond | blond | blond | blond |

| Example No. Dyes | 76 | 77 | 78 | 79 |
|---|---|---|---|---|
| | (Quantity of dye in grams) | | | |
| K1 [sic - Tr.] | 0.20 | 0.20 | 0.20 | 0.20 |
| E8 | 0.15 | | 0.20 | |
| E10 | 0.30 | | | |
| E11 | | 0.30 | | |
| E12 | | | 0.30 | |
| E14 | | | | 0.30 |
| E15 | | 0.20 | | 0.18 |
| K25 | 0.30 | 0.30 | | 0.30 |
| K26 | | | 0.35 | |
| Dyeing result | red-brown | red-brown | red-brown | red-brown |

Examples 80 to 86

Hair Colorants

Dye carriers in cream form and having the following composition were prepared:

| | |
|---|---|
| X g | of 1,3-dihydroxy-4-(thiophen-2-yl)benzene (coupler K2) |
| U g | of developer E8 to E15 as per Table 2 |
| Y g | of coupler K11 to K33 as per Table 3 |
| Z g | of direct dye D2 or D3 as per Table 4 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100 g | water |

Just before use, 30 g of the foregoing coloring solution was mixed with 30 g of a 6% aqueous solution of hydrogen peroxide. The mixture was then applied to bleached hair. After an exposure time of 30 mm at 40° C., the hair was rinsed with water, washed with a commercial shampoo and dried. Table 8 shows the coloring results.

TABLE 8

Hair Colorants

| Example No. | 80 | 81 | 83 | 84 | 85 | 86 |
|---|---|---|---|---|---|---|
| Dyes | (Quantity of dye in grams) | | | | | |
| K1 [sic] | 1.10 | 1.10 | 0.6 | 0.20 | 0.40 | 0.40 |
| E8 | 1.50 | | | | | |
| E13 | | 1.60 | | | | 0.70 |
| E15 | | | 1.80 | 0.70 | 0.70 | |
| K12 | 0.60 | | | | | |
| K13 | 0.70 | 1.50 | 1.25 | 0.18 | 0.18 | 0.18 |
| K23 | | | 0.05 | 0.10 | 0.10 | 0.10 |
| K31 | | | | 0.60 | 0.20 | |
| D3 | | | | | 0.10 | |
| D2 | | | | | 0.10 | 0.10 |
| Dyeing result | black | black | black | brown | brown | brown |

Unless otherwise indicated, all percentages given above are by weight.

The invention claimed is:

1. A 1,3-Dihydroxy-4-heteroarylbenzene derivative of formula (I), or a physiologically tolerated, water-soluble salt thereof:

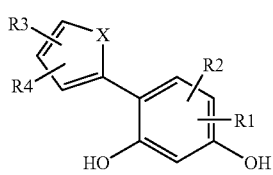

(I)

wherein X denotes oxygen, sulfur or N—R5;
R1 and R2 are equal or different and, independently of each other, denote hydrogen, a halogen atom, a hydroxyl group, a $C_1$–$C_4$-alkoxy group, a $C_1$–$C_4$-hydroxyalkoxy group, a $C_1$–$C_6$-alkyl group, a $C_1$–$C_4$-alkylthioether group, a trifluoromethyl group, a —Si(CH$_3$)$_3$ group, a $C_1$–$C_4$-hydroxyalkyl group or a $C_2$–$C_4$-dihydroxyalkyl group;
R3 and R4 are equal or different and, independently of each other, denote hydrogen, a hydroxyl group, a halogen atom, a cyano group, a $C_1$–$C_4$-alkoxy group, a $C_1$–$C_6$-alkyl group, a $C_1$–$C_4$-alkylthioether group, a mercapto group, a nitro group, an amino group, a $C_1$–$C_4$-alkylamino group, a di($C_1$–$C_4$)alkylamino group, a —C(O)H group, a —C(O)CH$_3$ group, a —C(O)CF$_3$ group, a —Si(CH$_3$)$_3$ group, a $C_1$–$C_4$-hydroxyalkyl group or a $C_2$–$C_4$-dihydroxyalkyl group; and
R5 denotes hydrogen, a $C_1$–$C_6$-alkyl group, a $C_2$–$C_4$-hydroxyalkyl group, a phenyl group or an acetyl group;
with the proviso that at least one of R1 to R4 is not hydrogen when X denotes oxygen.

2. The 1,3-Dihydroxy-4-heteroarylbenzene derivative as defined in claim 1, wherein (i) at least one of R1, R2, R3 and R4 denote hydrogen and X denotes sulfur or oxygen or (ii) R1 and R2 simultaneously denote hydrogen and X denotes sulfur.

3. The 1,3-Dihydroxy-4-heteroarylbenzene derivative as defined in claim 1, which is selected from the group consisting of 1,3-dihydroxy-4-(thiophen-2-yl)-benzene, 1,3-dihydroxy-4-(5-nitrothiophen-2-yl)benzene, 1,3-dihydroxy-4-(3-methylthiophen-2-yl)benzene and the physiologically tolerated salts thereof.

4. A 1,3-Dihydroxybenzene derivative of formula (Ia), or a physiologically tolerated, water-soluble salt thereof:

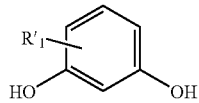

(I'a)

wherein R'1 denotes a substituted pyridyl group, a pyrimidyl group, a group of formula (IIa):

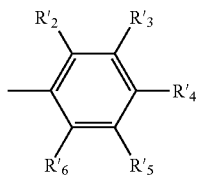

(IIa)

or a group of formula (IIIa):

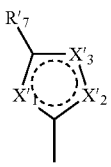

(IIIa)

wherein R'2, R'3, R'4, R'5 and R'6, independently of each other, denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkylthioether group, a mercapto group, a nitro group, an amino group, a $C_1$–$C_4$-alkylamino group, a hydroxy-($C_1$–$C_4$)alkylamino group, a di($C_1$–$C_4$)alkylamino group, a di[hydroxy($C_1$–$C_4$)-alkyl]amino group, a dihydroxy-($C_3$–$C_4$->)alkylamino group, a [hydroxy-($C_1$–$C_4$)alkyl]-$C_1$–$C_4$-alkylamino group, a trifluoromethyl group, a —C(O)H group, a —C(O)$CH_3$ group, a —C(O)$CF_3$ group, a —Si($CH_3$)$_3$ group, a $C_1$–$C_4$-hydroxyalkyl group or a $C_2$–$C_4$-dihydroxyalkyl group, or two adjacent R'2 to R'6 groups form an —O—$CH_2$—O— bridge;

X'1 denotes sulfur, nitrogen, oxygen, C—R'9 or N—R'8;
X'2 denotes sulfur, nitrogen, oxygen, C—R'10 or N—R'8;
X'3 denotes sulfur, nitrogen, oxygen, C—R'11 or N—R'8;
R'7, R'9, R'10 and R'11, independently of each other, denote hydrogen, a halogen atom, a cyano group, a $C_1$–$C_4$-alkoxy group, a $C_1$–$C_6$-alkyl group, a $C_1$–$C_4$-alkylthioether group, a mercapto group, a nitro group, an amino group, a $C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)$CH_3$ group, a —C(O)$CF_3$ group, an —Si($CH_3$)$_3$ group, a $C_1$–$C_4$-hydroxyalkyl group or a $C_3$–$C_4$-dihydroxyalkyl group; and R'8 denotes hydrogen, a $C_1$–$C_6$-alkyl group, a $C_2$–$C_4$-hydroxyalkyl group, a phenyl group or an acetyl group, provided that at least one and at the most two of the X'1 to X'3 groups denote CR'9, C—R'10 or C—R'11 and at the most one of the X'1 to X'3 groups denotes sulfur, oxygen or N—R'8, and R'1 does not stand for a phenyl group or hydroxyphenyl group and provided that, when R'1 is the group of the formula IIIa, X'2 is not oxygen when X'1 and X'3 are CH and R'7 is hydrogen and also X'1 is not oxygen when X'2 and X'3 are CH and R'7 is hydrogen.

5. A composition for oxidative dyeing of keratin fibers containing a combination of developer substance and coupler substance, wherein said coupler substance comprises at least one 1,3-dihydroxy-4-heteroarylbenzene derivative of formula (I), or a physiologically tolerated, water-soluble salt thereof:

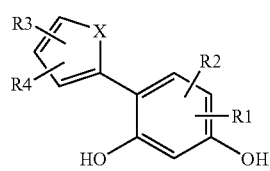

(I)

wherein X denotes oxygen, sulfur or N—R5;
R1 and R2 are equal or different and, independently of each other, denote hydrogen, a halogen atom, a hydroxyl group, a $C_1$–$C_4$-alkoxy group, a $C_1$–$C_4$-hydroxyalkoxy group, a $C_1$–$C_6$-alkyl group, a $C_1$–$C_4$-alkylthioether group, a trifluoromethyl group, a —Si($CH_3$)$_3$ group, a $C_1$–$C_4$-hydroxyalkyl group or a $C_2$–$C_4$-dihydroxyalkyl group;
R3 and R4 are equal or different and, independently of each other, denote a hydroxyl group, a halogen atom, a cyano group, a $C_1$–$C_4$-alkoxy group, a $C_1$–$C_8$-alkyl group, a $C_1$–$C_4$-alkylthioether group, a mercapto group, a nitro group, an amino group, a $C_1$–$C_4$-alkylamino group, a di($C_1$–$C_4$)alkylamino group, a —C(O)H group, a —C(O)$CH_3$ group, a —C(O)$CF_3$ group, a di($CH_3$)$_3$ group, a $C_1$–$C_4$-hydroxyalkyl group or a $C_2$–$C_4$-dihydroxyalkyl group; and R5 denotes hydrogen, a $C_1$–$C_6$-alkyl group, a $C_2$–$C_4$-hydroxyalkyl group, a phenyl group or an acetyl group.

6. The 1,3-Dihydroxy-4-heteroarylbenzene derivative as defined in claim 5, wherein (i) at least one of R1, R2, R3 and R4 denote hydrogen and X denotes sulfur or oxygen or (ii) R1 and R2 simultaneously denote hydrogen and X denotes sulfur.

7. The 1,3-Dihydroxy-4-heteroarylbenzene derivative as defined in claim 5, which is selected from the group consisting of 1,3-dihydroxy-4-(thiophen-2-yl)-benzene, 1,3-dihydroxy-4-(5-nitrothiophen-2-yl)benzene, 1,3-dihydroxy-4-(3-methylthiophen-2-yl)benzene and 1,3-dihydroxy-4-(furan-2-yl)-benzene.

8. The composition as defined in claim 5, containing from 0.005 to 20 wt. % of said at least one 1,3-dihydroxy-4-heteroarylbenzene derivative.

9. The composition as defined in claim 5, wherein said developer substance is selected from the group consisting of 1,4-diaminobenzene; 1,4-diamino-2-methylbenzene; 1,4-diamino-2,6-dimethylbenzene; 1,4-diamino-3,5-diethylbenzene; 1,4-diamino-2,5-dimethylbenzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl) benzene; 2,5-diaminobiphenyl; 1,4-diamino-2-methoxymethylbenzene; 1,4-diamino-2-aminomethylbenzene; 1,4-diamino-2-hydroxymethylbenzene; 1,4-diamino-2-(2-hydroxyethoxy)-benzene; 2-[2-(acetylamino)-ethoxy]-1,4-diaminobenzene; 4-phenylaminoaniline; 4-dimethylaminoaniline; 4-diethylaminoaniline; 4-dipropylaminoaniline; 4-[ethyl-(2-hydroxyethyl)amino]-aniline; 4-[di(2-hydroxy-ethyl)-amino]aniline; 4-[di(2-hydroxyethyl)amino]-2-methylaniline; 4-[(2-methoxyethyl)-aminolaniline; 4-[(3-hydroxypropyl)amino]-aniline; 4-[(2,3-dihydroxypropyl)aminoaniline; 1,4-diamino-2-(1-hydroxyethyl)-benzene; 1,4-diamino-2-(2-hydroxyethyl) benzene; 1,4-diamino-2-(1-methylethyl)-benzene; 1,3-bis-[(4-aminophenyl)(2-hydroxyethyl)amino]-2-propanol; 1,4-bis-[(4-amino-phenyl)amino]butane; 1,8-bis-(2,5-diaminophenoxy)-3,6-dioxaoctane; 4-aminophenol; 4-amino-3-methylphenol; 4-amino-3-(hydroxymethyl)phenol; 4-amino-3-fluorophenol; 4-methylaminophenol; 4-amino-2-(aminomethyl)phenol; 4-amino-2-(hydroxymethyl)phenol; 4-amino-2-fluorophenol; 4-amino 2-[(2-hydroxyethyl)amino]-methylphenol; 4-amino-2-methylphenol; 4-amino 2-(methoxymethyl)phenol; 4-amino-2-(2-hydroxyethyl)phenol; 5-aminosalicylic acid; 2,5-diaminopyridine; 2,4,5,6-tetraamino-pyrimidine; 2,5,6-triamino 4-(1H)-pyrimidone, 4,5-diamino-1-(2-hydroxyethyl)-1H-pyrazole; 4,5-diamino-1-(1-methylethyl)-1H-pyrazole; 4,5-diamino-1-[(4-methylphenyl)-methyl]-1H-pyrazole; 1-[(4-chlorophenyl)methyl]-4,5-diamino-1H-pyrazole; 4,5-diamino-1-methyl-1H-pyrazole; 2-aminophenol; 2-amino-6-methylphenol; 2-amino-5-methylphenol and 1,2,4-trihydroxybenzene.

10. The composition as defined in claim 5, wherein, in addition to said at least one 1,3-dihydroxy-4-heteroarylbenzene derivative, said coupler substance includes at least one member selected from the group consisting of N-(3-dimethylaminophenyl)urea; 2,6-diaminopyridine; 2-amino-4-[(2-hydroxyethyl)-amino]anisole; 2,4-diamino-1-fluoro-5-methylbenzene; 2,4-diamino-1-methoxy-5-methylbenzene; 2,4-diamino-1-ethoxy-5-methyl-benzene; 2,4-diamino-1-(2-hydroxyethoxy)-5-methylbenzene; 2,4-di[(2-hydroxyethyl)-amino]-1,5-dimethoxybenzene; 2,3-diamino-6-methoxypyridine; 3-amino-6-methoxy-2-(methylamino) pyridine; 2,6-diamino-3,5-dimethoxypyridine; 3,5-diamino- 2,6-dimethoxypyridine; 1,3-diaminobenzene; 2,4-diamino-1-(2-hydroxyethoxy)benzene; 1,3-diamino-4-(2,3-dihydroxypropoxy)benzene; 1,3-diamino-4-(3-hydroxypropoxy)benzene; 1,3-diamino-4-(2-methoxyethoxy)-benzene; 2,4-diamino-1,5-di(2-hydroxyethoxy)benzene; 1-(2-aminoethoxy)-2,4-diaminobenzene; 2-amino-1-(2-hydroxyethoxy)-4-methyl-aminobenzene; 2,4-diaminophenoxyacetic acid; 3-[di(2-hydroxyethyl)amino]aniline; 4-amino-2-di[(2-hydroxyethyl)amino]-1-ethoxybenzene; 5-methyl-2-(1-methylethyl)phenol; 3-[(2-hydroxyethyl)amino]aniline; 3[(2-aminoethyl)-amino]aniline; 1,3-di-(2,4-diaminophenoxy)propane; di(2,4-diaminophenoxy)methane; 1,3-diamino-2,4-dimethoxybenzene; 2,6-bis(2-hydroxyethyl)aminotoluene; 4-hydroxyindole; 3-dimethylaminophenol; 3-diethyl-aminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichloro-phenol; 3-amino-2-methylphenol; 3-amino-2-chloro-6-methylphenol; 3-aminophenol; 2-[(3-hydroxyphenyl)amino]acetamide; 5-[(2-hydroxyethyl)-amino]-4-methoxy-2-methylphenol; 5-[(2-hydroxyethyl)amino]-2-methylphenol; 3[(2-hydroxyethyl)-amino]phenol; 3-[(2-methoxyethyl)amino]phenol; 5-amino-2-ethylphenol; 5-amino-2-methoxyphenol; 2-(4-amino-2-hydroxyphenoxy)ethanol; 5-[(3-hydroxypropyl)amino]-2-methylphenol; 3-[(2,3-dihydroxypropyl)amino]-2-methylphenol; 3-[(2-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; 1,2-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylene-dioxyaniline; 5-[(2-hydroxyethyl)amino]-1,3-benzodioxole; 6-bromo-1-hydroxy-3,4-methylenedioxybenzene; 3,4-diaminobenzoic acid; 3,4-dihydro-6-hydroxy-1,4-(2H)benzoxazine; 6-amino-3,4-dihydro-1,4-(2H)-benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

11. The composition as defined in claim 5, containing from 0.005 to 20 wt. % of a total amount of said developer substance and said coupler substance, based on a total amount of said composition.

12. The composition as defined in claim 5, further comprising at least one direct dye compound.

13. The composition as defined in claim 5, having a pH of 6.5 to 11.5.

14. The composition as defined in claim 5, consisting of a hair colorant.

15. A composition for dyeing keratin fibers containing a combination of developer substance and coupler substance, wherein said coupler substance comprises at least one 1,3-dihydroxybenzene derivative of formula (Ia), or a physiologically tolerated, water-soluble salt thereof:

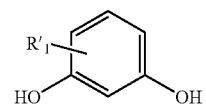

(I'a)

wherein R'1 denotes a substituted pyridyl group, a pyrimidyl group, a group of formula (IIa):

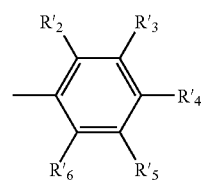

(IIa)

or a group of formula (IIIa):

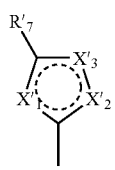

(IIIa)

wherein R'2, R'3, R'4, R'5 and R'6, independently of each other, denote hydrogen, a halogen atom, a cyano group, a hydroxyl group, a $C_1$–$C_4$-alkoxy group, a $C_1$–$C_4$— hydroxyalkoxy group, a $C_1$–$C_6$-alkyl group, a $C_1$–$C_4$-alkylthioether group, a mercapto group, a nitro group, an amino group, a $C_1$–$C_4$-alkylamino group, a hydroxy-($C_1$–$C_4$)alkylamino group, a di($C_1$–$C_4$)-alkylamino group, a di[hydroxy($C_1$–$C_4$)-alkyl]amino group, a dihydroxy-($C_3$–$C_4$-alkylamino group, a [hydroxy-($C_1$–$C_4$)-alkyl]-$C_1$–$C_4$-alkylamino group, a trifluoromethyl group, a —C(O)H group, a —C(O)CH$_3$ group, a —C(O)CF$_3$ group, a —Si(CH$_3$)$_3$ group, a $C_1$–$C_4$-hydroxyalkyl group or a $C_2$–$C_4$-dihydroxyalkyl group, or two adjacent R2 to R6 groups form an —O—CH$_2$-bridge;

X'1 denotes sulfur, nitrogen, oxygen, C—R'9 or N—R'8;
X'2 denotes sulfur, nitrogen, oxygen, C—R'10 or N—R'8;
X'3 denotes sulfur, nitrogen, oxygen, C—R'11 or N—R'8;
R'7, R'9, R'10 and R'11, independently of each other, denote hydrogen, a halogen atom, a cyano group, a $C_1$–$C_4$-alkoxy group, a $C_1$–$C_6$-alkyl group, a $C_1$–$C_4$-alkylthioether group, a mercapto group, a nitro group, an amino group, a $C_1$–$C_4$-alkylamino group, a di($C_1$–$C_4$)-alkylamino group, a di($C_1$–$C_4$-hydroxyalkyl)amino group, a $C_1$–$C_4$-hydroxyalkylamino group, a trifluoromethyl group, a —C(O)CH$_3$ group, a —C(O)CF$_3$ group, an —Si(CH$_3$)$_3$ group, a $C_1$–$C_4$-hydroxyalkyl group or a $C_3$–$C_4$-dihydroxyalkyl group; and R'8 denotes hydrogen, a $C_1$–$C_6$-alkyl group, a $C_2$–$C_4$-hydroxyalkyl group, a phenyl group or an acetyl group, provided that at least one and at the most two of the X'1 to X'3 groups denote C—R'9, C—R'10 or C—R'11 and at the most one of the X'1 to X'3 groups denotes sulfur, oxygen or N—R'8, and R'1 does not stand for a phenyl group or hydroxyphenyl group.

16. The composition as defined in claim 15, wherein (i) X'2 denotes C—R'10 and X'1 denotes sulfur and X'3 denotes C—R'11 or X'1 denotes C—R'9 and X'3 denotes sulfur, or (ii) X'2 denotes C—R10 and X'1 denotes sulfur and X'3 denotes C—R'11 or X'1 denotes C—R'9 and X'3 denotes sulfur and at least one of the R'9 to R'11 groups denotes hydrogen.

17. The composition as defined in claim 15, and wherein said at least one 1,3-dihydroxybenzene derivative is selected from the group consisting of 1,3-dihydroxy-4-(thiophen-2-yl)benzene, 1,3-dihydroxy-4-(5-nitro-thiophen-2-yl)-benzene, 1,3-dihydroxy-4-(3-methyl-thiophen-2-yl)benzene, 1,3-dihydroxy-4-(furan-2-yl)benzene, 1,3-dihydroxy-5-(5-chloro-thiophen-2-yl)-benzene, 1,3-dihydroxy-5-(3-methylthiophen-2-yl)-benzene and 1,3-dihydroxy-4-(thiophen-3-yl)-benzene and 1,3-dihydroxy-5-(thiophen-3-yl)-benzene.

18. The composition as defined in claim 15, containing from 0.005 to 20 wt. % of said at least one 1,3 dihydroxybenzene derivative.

19. The composition as defined in claim 15, wherein said developer substance is selected from the group consisting of 1,4-diamino-benzene; 1,4-diamino-2-methyl-benzene; 1,4-diamino-2,6-dimethylbenzene; 1,4-diamino-3,5-diethylbenzene; 1,4-diamino-2,5-dimethylbenzene; 1,4-diamino-2,3-dimethylbenzene; 2-chloro-1,4-diaminobenzene; 1,4-diamino-2-(thiophen-2-yl)benzene; 1,4-diamino-2-(thiophen-3-yl)benzene; 1,4-diamino-2-(pyridin-3-yl)benzene; 2,5-diamino-biphenyl; 1,4-diamino-2-methoxymethylbenzene; 1,4-diamino-2-aminomethyl-benzene; 1,4-diamino-2-hydroxymethylbenzene; 1,4-diamino-2-(2-hydroxy-ethoxy)-benzene; 2-[2-(acetylamino)ethoxy]-1,4-diaminobenzene; 4-phenyl-aminoaniline; 4-dimethylaminoaniline: 4-diethyl-aminoaniline; 4-dipropylamino-aniline; 4-[ethyl-(2-hydroxyethyl)amino]aniline; 4-[di(2-hydroxyethyl)-amino]-aniline; 4-[di(2-hydroxyethyl)amino]-2-methylaniline; 4-[(2-methoxyethyl)-aminolaniline; 4[(3-hydroxypropyl)amino]aniline; 4[(2,3-dihydroxypropyl)-aminoaniline; 1,4-diamino-2-(1-hydroxyethyl)benzene; 1,4-diamino-2-(2-hydroxyethyl) benzene; 1,4-diamino-2-(1-methylethyl)benzene; 1,3-bis-[(4-aminophenyl)(2-hydroxyethyl)amino]-2-propanol; 1,4-bis-[(4-amino phenyl)amino]butane; 1,8-bis-(2,5-diaminophenoxy)-3,6-dioxaoctane; 4-aminophenol; 4-amino-3-methylphenol; 4-amino-3-(hydroxymethyl)phenol; 4-amino-3-fluorophenol; 4-methylaminophenol; 4-amino-2-(aminomethyl)phenol; 4-amino-2-(hydroxymethyl)phenol; 4-amino-2-fluorophenol; 4-amino-2-[(2-hydroxyethyl)-amino]-methylphenol; 4-amino-2-methylphenol; 4-amino-2-(methoxymethyl)-phenol; 4-amino-2-(2-hydroxyethyl)phenol; 5-aminosalicylic acid; 2,5-diaminopyridine; 2,4,5,6-tetraamino-pyrimidine; 2,5,6-triamino-4-(1H)-pyrimidone; 4,5-diamino-1-(2-hydroxyethyl)-1H-pyrazole; 4,5-amino-1-(1-methylethyl)-1H-pyrazole; 4,5-diamino-1-[(4-methylphenyl)-methyl]-1H-pyrazole; 1-[(4-chloro-phenyl)-methyl]-4,5-diamino-1H-pyrazole; 4,5-diamino-1-methyl-1H-pyrazole; 2-aminophenol; 2-aminomethylphenol; 2-amino-5-methylphenol and 1,2,4-trihydroxybenzene.

20. The composition as defined in calm 15, wherein, in addition to said at least one 1,3-dihydroxybenzene derivative, said coupler substance includes at least one member selected from the group consisting of N-(3-dimethylaminophenyl)-urea; 2,6-diaminopyridine; 2-amino-4-[(2-hydroxy-ethyl)-amino]anisole; 2,4-diamino-1-fluoro-5-methylbenzene; 2,4-diamino-1-methoxy-5-methyl-benzene; 2,4-diamino-1-ethoxy-5-methylbenzene; 2,4-diamino-1-(2-hydroxyethoxy)-5-methylbenzene; 2,4-di[(2-hydroxyethyl)-amino]-1,5-dimethoxybenzene; 2,3-diamino-6-methoxypyridine; 3-amino-6-methoxy-2-(methylamino) pyridine; 2,6-diamino-3,5-dimethoxypyridine; 3,5-diamino-2,6-dimethoxypyridine; 1,3-diaminobenzene; 2,4-diamino-1-(2-hydroxyethoxy)benzene; 1,3-diamino-4-(2,3-dihydroxypropoxy)-benzene; 1,3-diamino-4-(3-hydroxypropoxy)benzene; 1,3-diamino-4-(2-methoxyethoxy)-benzene; 2,4-diamino-1,5-di(2-hydroxyethoxy)-benzene; 1-(2-aminoethoxy)-2,4-diaminobenzene; 2-amino-1-(2-hydroxyethoxy)-4-methyl-aminobenzene; 2,4-diaminophenoxyacetic acid; 3-[di(2-hydroxyethyl)-amino]aniline; 4-amino-2-di[(2-hydroxyethyl)amino]-1-ethoxybenzene; 5-methyl-2-(1-methylethyl)phenol; 3-[(2-hydroxyethyl)amino]aniline; 3[(2-aminoethyl)-amino]aniline; 1,3-di-(2,4-diamino-phenoxy)propane; di(2,4-diaminophenoxy)-methane; 1,3-diamino-2,4-dimethoxybenzene; 2,6-bis(2-hydroxyethyl)aminotoluene; 4-hydroxyindole; 3-dimethylaminophenol; 3-diethyl-aminophenol; 5-amino-2-methylphenol; 5-amino-4-fluoro-2-methylphenol; 5-amino-4-methoxy-2-methylphenol; 5-amino-4-ethoxy-2-methylphenol; 3-amino-2,4-dichlorophenol; 5-amino-2,4-dichlorophenol; 3-amino-2-methylphenol; 3-amino-2-chloro-6-methylphenol; 3-aminophenol; 2-[(3-hydroxy-phenyl)amino]acetamide; 5-[(2-hydroxyethyl)amino]-4-methoxy-2-methylphenol; 5-[(2-hydroxyethyl)amino]-2-methylphenol; 3-[(2-hydroxyethyl)-amino]phenol; 3-[(2-methoxyethyl)amino]-phenol; 5-amino-2-ethylphenol; 5-amino-2-methoxyphenol; 2-(4-amino-2-hydroxyphenoxy)ethanol; 5-[(3-hydroxypropyl) amino]-2-methylphenol; 3-[(2,3-dihydroxypropyl)amino]-2-methylphenol; 3-[(2-hydroxyethyl)amino]-2-methylphenol; 2-amino-3-hydroxypyridine; 2,6-dihydroxy-3,4-dimethylpyridine; 5-amino-4-chloro-2-methylphenol; 1-naphthol; 2-methyl-1-naphthol; 1,5-dihydroxynaphthalene; 1,7-dihydroxynaphthalene; 2,3-dihydroxynaphthalene; 2,7-dihydroxynaphthalene; 2-methyl-1-naphthol acetate; 1,3-dihydroxybenzene; 1-chloro-2,4-dihydroxybenzene; 2-chloro-1,3-dihydroxybenzene; $_{1,2}$-dichloro-3,5-dihydroxy-4-methylbenzene; 1,5-dichloro-2,4-dihydroxybenzene; 1,3-dihydroxy-2-methylbenzene; 3,4-methylenedioxyphenol; 3,4-methylene-dioxyaniline; 5-[(2-hydroxyethyl) amino]-1,3-benzodioxole; 6-bromo-1-hydroxy-3,4-methylenedioxybenzene; 3,4-diaminobenzoic acid; 3,4-dihydro-6-hydroxy-1,4-(2H)benzoxazine; 6-amino-3,4-dihydro-1,4-(2H)benzoxazine; 3-methyl-1-phenyl-5-pyrazolone; 5,6-dihydroxyindole; 5,6-dihydroxyindoline; 5-hydroxyindole; 6-hydroxyindole; 7-hydroxyindole and 2,3-indolinedione.

21. The composition as defined in claim 15, containing from 0.005 to 20 wt. % of a total amount of said developer substance and said coupler substance, based on a total amount of said composition.

22. The composition as defined in claim 15, further comprising at least one direct dye compound.

23. The composition as defined in claim 15, having a pH of 6.5 to 11.5.

24. The composition as defined in claim 15, consisting of a hair colorant.

* * * * *